United States Patent
Süling et al.

(10) Patent No.: US 6,245,944 B1
(45) Date of Patent: *Jun. 12, 2001

(54) PROCESS FOR PRODUCING SUBSTITUTED INDANONES

(75) Inventors: Carsten Süling, Odenthal; Heike Gregorius, Bad Kreuznach; Walter Dobler, Heidelberg; Roland Hingmann, Ladenburg; Bernhard Rieger; Ulf Dietrich, both of Ulm; Jürgen Matthäus Wagner, Dornstadt; Hans-Joachim Müller, Grünstadt, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/202,091
(22) PCT Filed: Jun. 11, 1997
(86) PCT No.: PCT/EP97/03029
  § 371 Date: Dec. 9, 1998
  § 102(e) Date: Dec. 9, 1998
(87) PCT Pub. No.: WO97/49661
  PCT Pub. Date: Dec. 31, 1997

(30) Foreign Application Priority Data

Jun. 21, 1996 (DE) ............................................. 196 24 828

(51) Int. Cl.$^7$ ................................................ C07C 45/46
(52) U.S. Cl. .................. 568/317; 568/309; 568/312; 568/315; 568/316
(58) Field of Search ................... 568/312, 315, 568/309, 316, 317, 326

(56) References Cited

U.S. PATENT DOCUMENTS

| 5,329,049 | 7/1994 | Weisse et al. | 568/319 |
| 5,360,936 | 11/1994 | Weisse et al. | 568/319 |
| 5,455,366 | 10/1995 | Rohrmann et al. | 556/8 |

FOREIGN PATENT DOCUMENTS 2084016 5/1993 (CA).
08012615 * 1/1996 (JP).

OTHER PUBLICATIONS

Kirk–Othmer, Encyclopedia of Chemical Technology, fourth edition, pp. 1042–1069, 1994.*

* cited by examiner

*Primary Examiner*—Sreeni Padmanabhan
(74) *Attorney, Agent, or Firm*—Keil & Weinkauf

(57) ABSTRACT

A process for preparing a compound of the formula I

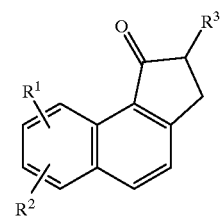

where $R^1$ and $R^2$ are hydrogen or $C_1$–$C_4$-alkyl and $R^3$ is $C_1$–$C_{10}$-alkyl, phenyl or $C_1$–$C_4$-alkyl-substituted phenyl, comprises reacting a compound II

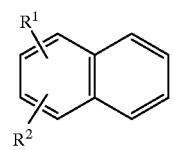

with a compound of the formula III

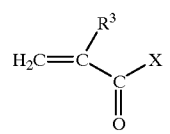

where X is chlorine, bromine or iodine, in the presence of a Friedel-Crafts catalyst in one step to give a compound I.

12 Claims, No Drawings

PROCESS FOR PRODUCING SUBSTITUTED INDANONES

This is the US National Stage Application of PCT/EP97/03029 filed Jun. 11, 1997.

The present invention relates to a process for preparing a compound of the formula I

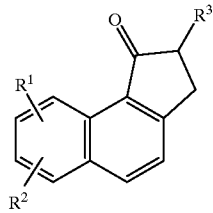

where $R^1$ and $R^2$ are hydrogen or $C_1$–$C_4$-alkyl and $R^3$ is $C_1$–$C_{10}$-alkyl, phenyl or $C_1$–$C_4$-alkyl-substituted phenyl.

Indanones of the general formula I are important precursors for metallocene complexes which are used as polymerization catalysts. For this purpose, the indanones are reduced and dehydrated; the resulting indene derivatives can be reacted with transition metals to give the corresponding metallocene complexes.

Various processes for preparing substituted indanones are known. EP-A1 549 900 describes the synthesis of a substituted benzindanone. In this case, the five-membered ring is constructed in a multistage synthesis by reaction with a malonic ester, alkaline hydrolysis of the diester, thermal decarboxylation, chlorination of the remaining carboxyl group and intramolecular Friedel-Crafts acylation. Owing to its large number of stages, the synthesis is technically very elaborate.

EP-A1 567 953 describes a synthesis of indanone derivatives in which the five-membered ring is constructed by reacting an appropriate benzene derivative with a substituted acrylic ester in liquid hydrogen fluoride. EP-A1 587 107 describes the preparation of 2-methylbenzindanone by reacting naphthalene with methacrylic anhydride in the presence of $BF_3$/hydrogen fluoride. These synthetic routes are also associated with considerable technical complexity because of the difficulty of handling extremely toxic hydrofluoric acid.

Another synthetic route for indanones is described in EP-A1 545 304. In this case, preparation takes place by reacting a benzene derivative with a-haloalkylpropionyl halides, preferably with a-bromoisobutyryl bromide. The disadvantage of this synthesis is the large amount of halogen-containing waste produced.

It is an object of the present invention to find a simple synthetic route for preparing benzindanones of the general formula I which overcomes the disadvantages of the known synthetic routes.

We have found that this object is achieved by a process for preparing a compound of the formula I

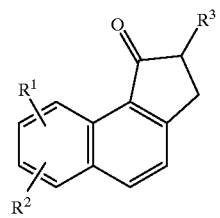

where $R^1$ and $R^2$ are hydrogen or $C_1$–$C_4$-alkyl and $R^3$ is $C_1$–$C_{10}$-alkyl, phenyl or $C_1$–$C_4$-alkyl-substituted phenyl, which comprises reacting a compound II

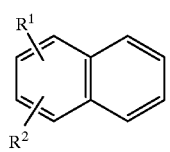

with a compound of the formula III

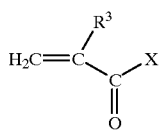

where X is chlorine, bromine or iodine, in the presence of a Friedel-Crafts catalyst in one step to give a compound I.

Reaction of compound II with a compound III may result in various isomers. However, the process according to the invention displays a pronounced regioselectivity so that usually only isomer I is observed.

In the indanone derivatives I which can be prepared by the process according to the invention, the substituents $R^1$ and $R^2$ may, besides hydrogen, be, for example, methyl, ethyl, isopropyl, n-propyl, n-butyl, isobutyl, sec-butyl or tert-butyl, with hydrogen being particularly preferred. Among the alkyl radicals, isopropyl should be particularly mentioned, but preferably only one of the radicals $R^1$ or $R^2$ is an alkyl radical.

The substituent $R^3$ is introduced via compound III into the target compounds. $R^3$ is preferably methyl or ethyl, particularly preferably methyl, but other $C_1$–$C_{10}$-alkyl radicals, the phenyl radical or $C_1$–$C_4$-alkyl-substituted phenyl radicals are also suitable. Suitable $C_1$–$C_{10}$-alkyl radicals are, besides the abovementioned $C_1$–$C_4$-alkyls, also the various isomeric pentyl, hexyl, heptyl, octyl, nonyl and decyl radicals. Suitable phenyl radicals are, besides the preferred unsubstituted phenyl radical, in particular phenyl radicals monosubstituted by methyl or ethyl.

The radical X in the compound III can be chlorine, bromine or iodine, and is preferably chlorine.

The catalyst used in the process according to the invention is a Friedel-Crafts catalyst. Suitable Friedel-Crafts catalysts are all conventional catalysts of this type, for example $AlCl_3$, $AlBr_3$, $BF_3$, $ZnCl_2$, $FeCl_3$, $SnCl_4$ and $SbCl_5$, preferably $AlCl_3$.

The Friedel-Crafts catalyst, especially $AlCl_3$, is generally employed in excess, preferably in an amount such that the molar ratio of catalyst to compound III is from 1 to 2, particularly preferably from 1 to 1.5, very particularly preferably from 1.05 to 1.3.

All conventional Friedel-Crafts solvents are suitable for the process according to the invention, although carbon disulfide is not very suitable, for example, because of its toxicity. Particularly suitable solvents are chlorinated hydrocarbons such as methylene chloride, 1,2-dichloroethane, 1,1,2,2-tetrachloroethane and chlorobenzene, particularly preferably methylene chloride.

The reaction is preferably carried out at from −30 to 0° C., particularly preferably from −20 to −10° C. However, at the end of the reaction, the temperature can be raised to complete the ring-closure reaction, eg. to 10–40° C., preferably to 20–30° C.

The pressure generally has a negligible effect on the reaction so that it is normally carried out under atmospheric pressure.

The process according to the invention is distinguished by simple technical manipulation (one-stage process) and small amounts of halogen-containing waste produced. In addition, it displays excellent regioselectivity and affords the required products in very good yields.

The following example illustrates the invention:

EXAMPLE

Preparation of

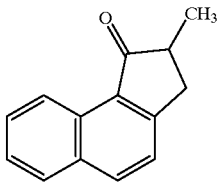

Freshly powdered aluminum chloride (13 g, 97 mmol) was dissolved in 42 ml of $CH_2Cl_2$ and cooled to −15° C. Methacryloyl chloride (97%, 8 ml, 8.6 g, 81 mmol) was added dropwise at such a rate that the temperature did not exceed −10° C. A solution of 10.4 g of naphthalene (81 mmol) in 42 ml of $CH_2Cl_2$ was then added dropwise at such a rate that the temperature did not exceed −10° C. The solution was stirred at −15° C. for 2 h and at room temperature for 2 h and then hydrolyzed with 300 ml of ice-water. Precipitated aluminum hydroxide gel was dissolved with a little HCl, and the organic phase was removed. The aqueous phase was then extracted three times with 80 ml of $CH_2Cl_2$, and the combined organic phases were washed with saturated $NaHCO_3$ solution and then with saturated NaCl solution and dried over $Na_2SO_4$.

The residue after evaporation of the $CH_2Cl_2$ was taken up in ethyl acetate and purified by filtration through a short silica gel column. Renewed evaporation of the solvent afforded a reddish viscous oil which slowly became solid. The $^1$H-NMR spectrum was consistent with the literature data (EP 0 545 304).

Formation of the isomeric 2-methyl-4,5-benzoindan-3-one, which was also produced in the synthesis in EP 0 545 304, and of 2-methyl-5,6-benzoindan-1-one was not observed.

Yield: 15.1 g.

We claim:

1. A regioselective process for preparing a compound of the formula I

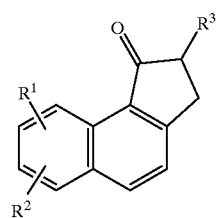

where $R^1$ and $R^2$ are hydrogen or $C_1$–$C_4$-alkyl and $R^3$ is $C_1$–$C_{10}$-alkyl, phenyl or $C_1$–$C_4$-alkyl-substituted phenyl, which comprises reacting a compound II

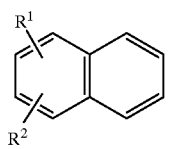

with a compound of the formula III

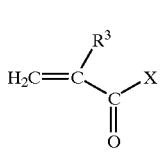

where X is chlorine, bromine or iodine, in the presence of a Friedel-Crafts catalyst selected from the group consisting of $AlCl_3$, $FeCl_3$ and $FeBr_3$, in a chlorinated hydrocarbon solvent at temperatures between −30 and 0° C. in one step to yield compound I.

2. A process as claimed in claim 1, wherein $R^1$ and $R^2$ are hydrogen.

3. A process as claimed in claim 1, wherein $R^3$ is methyl or ethyl.

4. A process as claimed in claim 1, wherein $AlCl_3$ is employed as said Friedel-Crafts catalyst.

5. A process as claimed in claim 1, wherein the molar ratio of $AlCl_3$ to compound III is from 1.0 to 1.5.

6. A process as claimed in claim 1, wherein said chlorinated hydrocarbon solvent is methylene chloride.

7. A regioselective process for preparing a compound of the formula I

I where $R^1$ and $R^2$ are hydrogen or $C_1$–$C_4$-alkyl and $R^3$ is $C_1$–$C_{10}$-alkyl, phenyl or $C_1$–$C_4$-alkyl-substituted phenyl, which comprises reacting a compound II

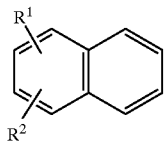

with a compound of the formula III

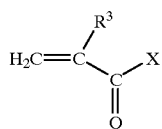

where X is chlorine, bromine or iodine, in the presence of a Friedel-Crafts catalyst selected from the group consisting of AlCl$_3$, FeCl$_3$ or FeBr$_3$ in a chlorinated hydrocarbon solvent in one step to yield compound I, wherein the temperature is maintained at from −30 to 0° C. at the beginning of the reaction and is raised to 10 to 40° C. at the end of the reaction.

8. A process as claimed in claim 7, wherein the temperature at the beginning of the reaction is maintained at from −20 to −10° C.

9. A process as claimed in claim 7, wherein the temperature is raised to 20 to 30° C. at the end of the reaction.

10. A process as claimed in claim 7, wherein said Friedel-Crafts catalyst is AlCl$_3$.

11. A process as claimed in claim 10, wherein the molar ratio of AlCl$_3$ to compound III is from 1.0 to 1.5.

12. A process as claimed in clain 7, wherein said chlorinated hydrocarbon solvent is methylene chloride.

* * * * *